United States Patent
Evtodienko et al.

(10) Patent No.: US 6,638,480 B2
(45) Date of Patent: Oct. 28, 2003

(54) HIGH SENSITIVITY TEST SYSTEM FOR THE COLORIMETRIC DETERMINATION OF SPECIFIC GRAVITY OR TOTAL DISSOLVED SOLIDS IN AQUEOUS SAMPLES

(75) Inventors: Iouri Vladimirovich Evtodienko, Elkhart, IN (US); Eugenia Makowski, South Bend, IN (US); David A. N. Morris, Granger, IN (US)

(73) Assignee: Environmental Test Systems, Inc., Elkhart, IN (US)

( * ) Notice: Subject to any disclaimer, the term of this patent is extended or adjusted under 35 U.S.C. 154(b) by 73 days.

(21) Appl. No.: 09/729,157

(22) Filed: Dec. 1, 2000

(65) Prior Publication Data

US 2002/0102740 A1 Aug. 1, 2002

(51) Int. Cl.$^7$ ................................................ G01N 33/00
(52) U.S. Cl. ........................... 422/61; 422/58; 436/164; 436/169; 436/808
(58) Field of Search ............................. 422/56, 61, 58; 436/2, 74, 163, 164, 169, 808

(56) References Cited

U.S. PATENT DOCUMENTS

| | | | |
|---|---|---|---|
| 4,015,462 A | 4/1977 | Greyson et al. | |
| 4,076,502 A | 2/1978 | Dugle et al. | |
| 4,108,727 A | 8/1978 | Stiso et al. | |
| 4,318,709 A | 3/1982 | Falb et al. | |
| 4,376,827 A | 3/1983 | Stiso et al. | |
| 4,473,650 A | 9/1984 | Wang | |
| 4,532,216 A | 7/1985 | Wang | |
| 5,055,407 A | 10/1991 | Lau et al. | |
| 5,064,615 A | 11/1991 | Mangold et al. | |
| 5,106,752 A | 4/1992 | Mangold et al. | |
| 5,215,712 A | 6/1993 | Kawanishi et al. | |
| 5,302,531 A | 4/1994 | Bauer | |
| 5,320,969 A | 6/1994 | Bauer et al. | |
| 5,350,694 A | 9/1994 | Zimmerle | |
| 5,403,744 A | 4/1995 | Zimmerle | |
| 5,443,990 A | 8/1995 | Harako | |
| 5,565,363 A | 10/1996 | Iwata et al. | |
| 5,631,163 A | 5/1997 | Pugia et al. | |
| 5,705,393 A | * 1/1998 | Sakamoto et al. | 436/2 |
| 5,753,451 A | 5/1998 | Smith | |
| 5,858,788 A | 1/1999 | Habenstein | |
| 5,922,283 A | 7/1999 | Hsu | |
| 5,955,370 A | 9/1999 | Kell | |

FOREIGN PATENT DOCUMENTS

GB       2 382 506 A       2/1999

* cited by examiner

Primary Examiner—Lyle A. Alexander
(74) Attorney, Agent, or Firm—Barnes & Thornburg

(57) ABSTRACT

A highly sensitive and convenient test method, composition and device for the facile calorimetric determination of total dissolved solids in an aqueous sample having a low specific gravity is presented. The reagent composition comprises the mixture of a complex of a positively charged polyelectrolyte and a negatively charged indicator material, and an appropriate buffer system for maintaining the test system environment at an exact pH depending upon the indicator material selected. A preferable embodiment of this test system comprises the incorporation of the test composition into or with a solid state matrix material such as bibulous paper. The test system is particularly useful in the field testing of potable and recreational waters.

6 Claims, 1 Drawing Sheet

HIGH SENSITIVITY TEST SYSTEM FOR THE COLORIMETRIC DETERMINATION OF SPECIFIC GRAVITY OR TOTAL DISSOLVED SOLIDS IN AQUEOUS SAMPLES

FIELD OF THE INVENTION

The present invention relates to a facile and utilitarian colorimetric test method, composition and device for the determination of specific gravity or total dissolved solids in low specific gravity aqueous samples. Because of its ability to measure low specific gravity fluids, it is primarily directed to potable and recreational water samples such as those found in swimming pools, spas as well as natural water environments. It may however be advantageously used for determining specific gravity in other aqueous substances such as biological and other fluids containing ionic constituents.

The system is basically a field test but may have utility in analytical laboratories for screening and other applications requiring immediate results. The system comprises a composition and method that in its preferable format utilizes a carrier or matrix for retaining the test reagent and advantageously bringing the active ingredients into contact with the water sample to achieve a calorimetric readout result.

BACKGROUND OF THE INVENTION AND PRIOR ART

Total Dissolved Solids (TDS) is a term of art used extensively in the water quality area. The term describes itself very aptly—it is the total amount of inorganic and/or organic substances dissolved in a water sample. It is often described as the "total filterable residue" of a water sample since it is what remains in the water sample after the suspended or insoluble particulate materials are removed therefrom by a standardized filtration process. Potable and recreational waters usually contain primarily inorganic cationic species such as calcium, magnesium and sodium salts and equivalent amounts of anionic species such as chlorides, sulfates and carbonates.

Historically, TDS has been determined using either gravimetric procedures or estimated by using electrical conductivity measurements. The gravimetric procedure is commonly a laboratory methodology since it usually involves precisely determining the residue remaining (by weight) after drying the sample using standardized drying procedures. Electrical conductivity measurement methods are usually easier to utilize; however, they require a dedicated conductivity meter and commonly require extensive calibration and maintenance practices. They provide estimations of total dissolved solids from the measured conductivity of the dissolved ionic species.

The significance of TDS in determining water quality stems from the fact that high TDS can result in taste problems in the potable water area, and from chemical balance problems in the recreational water area.

More recently, in the medical area, methods have been discovered and developed to measure the specific gravity of body fluids using calorimetric procedures. Generally speaking, the samples being studied in this area are usually body or other biological fluids and have a specific gravity much higher than those found in the water quality area.

The term "specific gravity" is commonly used in the medical area as opposed to the term "total dissolved solids" as used in the water quality area. Numerous other terms similar to specific gravity are also used in the medical area. Terms such as "specific density", "ionic strength", "divalent cation strength", "osmolality", "nosmolarity", "ion concentration" and "osmotic pressure" are commonly encountered. Each of these terms has itself a specific chemical meaning and definition but for the purposes of describing medical test systems, the somewhat generic term "specific gravity" will be used. The specific gravity of an aqueous sample can be defined as the ratio of its weight to that of an equal volume of pure water.

The calorimetric analytical schemes used to determine the specific gravity of a body fluid in the medical area basically utilize a polyelectrolyte and an indicator means capable of creating a detectable color response resulting from an ion exchange between the polyelectrolyte and the ions in the aqueous sample. This color response is then correlated to specific gravity.

Polyelectrolytes are usually proprietary polymeric materials having pendant ionic groups. They are well known in the art and are used extensively in chemical ion exchange reactions requiring separation or removal of ionic species.

Human urine is the most common body fluid tested using these analytical schemes to determine specific gravity, and the importance of this test resides in its use to diagnose a situation involving electrolyte imbalance and its associated diseased states.

Prior to the development of these colorimetric methods for determining the specific gravity of body fluids, clinical chemistry methodologies employed cumbersome procedures, and utilized delicate instruments such as refractometers and other specialized devices.

It should be noted here that in addition to having different terminologies, the specific gravity of a body fluid is quite different from the specific gravity or TDS of a water sample. Body fluids such as urine usually have a range of from about 1.005 to 1.030 specific gravity which is equal to a TDS ppm range from 7,000 to 43,000. In contrast, recreational waters typically have a TDS ppm range of values from only 300 to 5,000. Further, potable waters have even lower TDS values of from about 100 to 1,000 ppm.

Because of the different ranges noted above, it has been found that the traditional colorimetric methods used in the medical area were incapable of detecting the very low specific gravity ranges found in the recreational and potable water area.

In contrast to these calorimetric prior art methodologies, it has been found that the present test composition, as will be described later, involves a very different reaction mechanism.

It should also be noted that while the term specific gravity is simply a comparison ratio and has no dimensional tag, the term TDS is usually reported as milligrams per liter (mg/L) or parts per million (ppm).

The prior art surrounding calorimetric specific gravity tests is both extensive and complicated. Most of this prior art involves patent publications and in an attempt to present at least representative patents involving this methodology, the following table is presented:

TABLE

Exemplary Prior Art

| Patent or Application | Positive Component | Negative Component | Comments |
|---|---|---|---|
| Present Invention | Strongly basic polyelectrolyte or anion exchange polymer | Dye that binds to or Complexes with the positive body | Strongly Buffered, Responds to monovalent and divalent ions Does not work by pH shift Three to ten times more sensitive than urine SG tests |
| U.S. Pat. No. 5,858,788 Habenstein | Benzethonium chloride and optional other quaternary compounds | Ions from buffer | Must have benzethonium chloride in formulation. |
| U.S. Pat. No. 5,403,744 Zimmerle | Dye that binds to the negative body | Strongly acidic polyelectrolyte | Uses a strongly acidic polyelectrolyte. Buffered at pH 3 or less. Does not work by pH shift in the case of the metachromatic dye |
| U.S. Pat. No. 4,318,709 Falb et al. | Acid (H+) | Weakly acidic polyelectrolyte | Requires titration by acid or base to 75–90% of equivalence. |
|  | Weakly basic polyelectrolyte | Base (OH—) |  |
| U.S. Pat. No. 4,473,650 Wang | Weakly basic polyelectrolyte | Strong organic acid | Requires titration in the range 20–60% |
| U.S. Pat. No. 4,532,216 Wang | Strong organic base, e.g. $R_4N+$ | Weakly acidic polyelectrolyte | Requires titration up to 50% |
| U.S. Pat. No. 4,376,827 Stiso et al. | Strongly basic polyelectrolyte | Ions from buffer | Works by pH shift |
|  | Ions from buffer | Strongly acidic polyelectrolyte | Works by pH shift |

As stated above the table, this listing is only representative and is being given to present a small window to the plethora of combinations and permutations surrounding the essential components used in current calorimetric specific gravity tests.

SUMMARY OF THE INVENTION

The method, composition and device of the present invention involves a highly sensitive reagent system for determining the specific gravity or total dissolved solids of an aqueous sample. The basic system comprises a. a complex of a positively charged polyelectrolyte polymer ($PCPP^{n+}$) and a negatively charged indicator material ($I^-$) and b. a buffer system sufficient to maintain the mixture at an exact predetermined pH during the contact and reaction thereof with the aqueous sample. This mixture or composition has been found to generate a color change in a low specific gravity sample depending upon the concentration of anions in the water sample.

To achieve this desired low range detection sensitivity the reagent components were chosen so as to contribute minimally to a background TDS response. A standard color chart or graph is then prepared by using a series of known TDS concentration samples and determining the color produced with the test method or device. Finally, the TDS value of an unknown sample is determined by comparison of the developed color with the standard color chart or instrumentally reading the color in a standardized reflectance calorimeter.

DESCRIPTION OF THE PREFERRED EMBODIMENTS

Figure 1A:
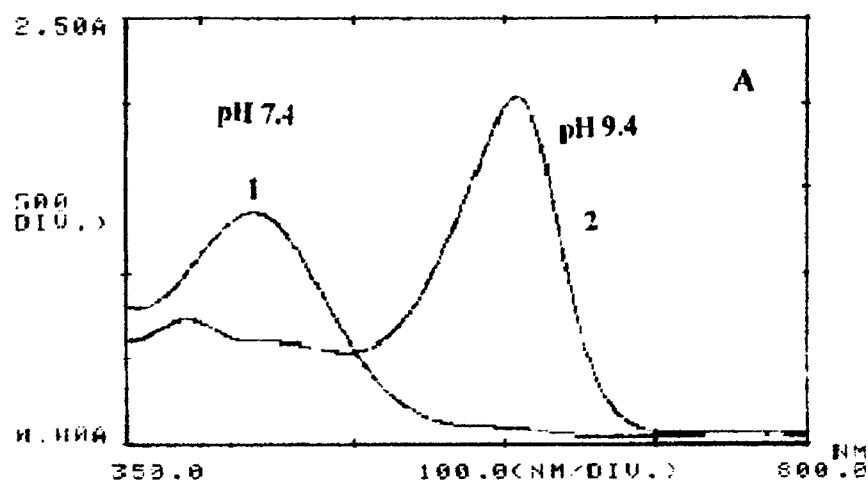
FIGS. 1A, 1B and 1C represent various conditions and responses of the present test system to TDS as described in the Examples that follow.

While certain of the basic building blocks of the present inventive test composition for determining TDS are similar to those used in the prior art medical test systems, the present system differs in that it is essentially a binding or complexing phenomenon between a positively charged polyelectrolyte polymeric ($PCPP^{n+}$) material and the negatively charged indicator material.

When the bound indicator contacts anions in the water sample, binding reversal occurs to release indicator into the reaction mixture causing the appearance of a color change. Since pH change is not a contributory factor in the test system, a strong buffer is employed to retain the reacting mixture at an optimized test reaction value. As used herein, the term color change means both the change in intensity of a single color and the change of one color to another.

The three necessary constituents of the present invention accordingly are 1. a positively charged polyelectrolyte polymeric material ($PCPP^{n+}$), 2. a negatively charged indicator material ($I^-$) and 3. a buffer material to maintain system pH at or below the pH indicator pKa.

The polyelectrolyte component of the present invention is a positively charged water-soluble substance having the capability of complexing with a negatively charged pH indicator as described in the following reaction 1:

Reaction 1—Formation of Reagent Complex

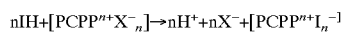

$$nIH + [PCPP^{n+}X^-_n] \rightarrow nH^+ + nX^- + [PCPP^{n+}I_n^-]$$

wherein $X^-$ is $OH^-$ or $Cl^-$.

Examples of the positively charged polymeric materials which have been found to be operable in the present invention are:
poly(4-vinylbenzyltrimethylammonium hydroxide);
poly(4-vinylbenzyltrimethylammonium chloride);
poly(diallyldimethylammonium hydroxide);
poly(diallyldimethylammonium chloride);
poly[bis(2-chloroethyl)ether-1,3 bis[3-(dimethylamino) propyl) urea]; and,
poly[oxyethylene(dimethylimino)-ethylene-(dimethylimino)ethylene dichloride]. These materials are polyelectrolytes with a positive charge on the nitrogen atom.

The second essential component of the present test system is the indicator material. These are primarily negatively charged pH sensitive dyestuffs capable of binding to the $PCPP^{n+}$ material, as shown in reaction 1 above. These color-generating substances preferably have transition intervals of from about pH 4.0 to pH 9.0. Exemplary of the indicator materials that can be used in the present reagent system are triphenylmethane or sulfonephthalein dyes such as thymol blue, m-cresol purple, xylenol blue, cresol red, phenol red, bromothymol blue and chlorophenol red.

The third essential component of the present reagent system comprises a buffer system of sufficient strength and/or concentration to maintain the test system at an exact pH but does not interfere with or contribute to the TDS response. Since the present test system depends on binding reversal rather than a pH change, however slight or small, the buffer system must be capable of maintaining the entire mixture of test composition and test sample to an exact predetermined pH. This pH is dependent upon the color transition range of the indicator material. The preferred buffer components must not have a significant effect on the test sensitivity.

Some buffer systems found to be suitable have components as follows: the base of the buffer system may be selected from the group consisting of imidazole; tris (hydroxymethyl)aminomethane; 2-amino-2-methyl 1,3-propanediol; bis(2-(hydroxyethyl)imino-tris (hydroxymethyl)methane; and, 1,3-bis[tris(hydroxymethyl) methylamino]propane and the acid selected from the group consisting of carboxylic acids, and preferably monocarboxylic acids, such as glycolic, lactic, benzoic, and acetic acids. This list is obviously representative and not intended to be a limitation to the selection of suitable buffers.

As previously stated, the reaction mechanism of the present invention involves the use of a complexed indicator material and polyelectrolyte polymer wherein the complexed indicator is released by contact with anions in the aqueous sample. Referring now to the reaction described in "Reaction 1" above, when thymol blue is used as an indicator (I), the uncomplexed form of this indicator is yellow at its acidic side pKa and blue at its basic side. In this reaction, the bulk pH of the mixture is maintained at the acidic or yellow side of the indicator pKa. Surprisingly, the [polymer/thymol blue] complexed indicator is now a blue color, even though the bulk pH is still at the acidic side of the indicator pKa.

Further, it was found that the anionic species (A⁻) of a TDS sample can replace the negatively charged indicator from [PCPP$^{n+}$ I$_n^-$] complex as shown in Reaction 2 next below.

Reaction 2. TDS Detection Using Thymol Blue as I⁻

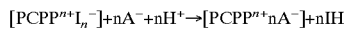

(BLUE) (YELLOW)

In this reaction the complexed indicator material, thymol blue, is displaced by anions and becomes protonated. It accordingly returns to its yellow uncomplexed form in the bulk phase. In the absence of the TDS anionic species the complex color is blue. With increasing TDS, that is, with increasing concentrations of anionic species, more of the uncomplexed indicator is formed. The increasing yellow form causes a color change from blue to green to yellow.

The concentration of the various components used in the present test system is of course dependent upon the individual component used; however, generally speaking the following ranges of concentrations of components may be used:

| | |
|---|---|
| PCPP$^{n+}$ | 0.10–30 g/L |
| Indicator Material | 0.01–3 g/L |
| Buffer | 0.30–75 mM |

Other inactive additives, such as thickening agents, stabilizers and surfactants, may also be used in the present test composition to achieve the desired format for presentation of the test system to the test sample.

Although the test reagent maybe used as a liquid system, a particularly preferable and advantageous format for the present test comprises the incorporation of the test reagent components into a matrix for holding the reagent in a dry, so-called solid state system, until presented to the aqueous test sample. When this is done, the reagent rehydrates, reacts with the anions in the test sample, and a color is developed in or on the matrix that can be compared to a standardized test color chart. The matrix may be bibulous paper, a synthetic polymeric material, or other membrane materials that in turn may be attached to more rigid plastic sheet materials, which act as a handle for ease of use of the test device.

Such devices are known in the art as reagent strip tests and are usually read visually or the color developed may be read and interpreted by an instrumental means such as a reflectometer. Likewise, if a liquid system is employed, the color developed may be read by visual comparison to standard color tubes or by a calorimeter.

Since the color produced in the reagent system relates to ionic species in the test sample rather than TDS directly, the color must be compared to standardized test samples which have been prepared using gravimetric procedures. A test comparison chart is then prepared which creates a direct correlation of color to TDS.

EXAMPLES

Example 1

This Example Describes a Liquid Reagent Composition Showing Color Change due to Indicator Binding With PCPP A test composition having thymol blue as a pH indicator, poly(4-vinlybenzyltrimethylammonium hydroxide)—(PVBA) as a positively charged polyelectrolyte polymer, and tris(hydroxymethyl)aminomethane (THAM)+glycolic acid as a pH buffer system was prepared by mixing the components in distilled water in the amount shown in Table 1. PVBA hydroxide was prepared from commercially available poly(4-vinylbenzyltrimethylammonium chloride) using strongly basic anion exchange resin. Glycolic acid (2 M solution) was added in the amount needed to establish a desirable pH of the composition.

TABLE 1

Liquid reagent composition and properties

| | Reagent Composition No. | | |
|---|---|---|---|
| | 1 | 2 | 3 |
| Reagent Composition And Characteristics | Without Polymer | Without Polymer | With Polymer |
| Bulk pH | 7.4 | 9.4 | 7.4 |
| PVBA mg/L (Polymer) | 0 | 0 | 150 |
| Thymol blue mg/L (Indicator) | 50 | 50 | 50 |
| THAM g/L (buffer) | 1.8 | 1.8 | 1.8 |
| Glycolic acid (pH adjustment) | + | + | + |
| Color and Indicator form | Yellow Uncomplexed | Blue Uncomplexed | Blue Complexed |

Figure 1B:
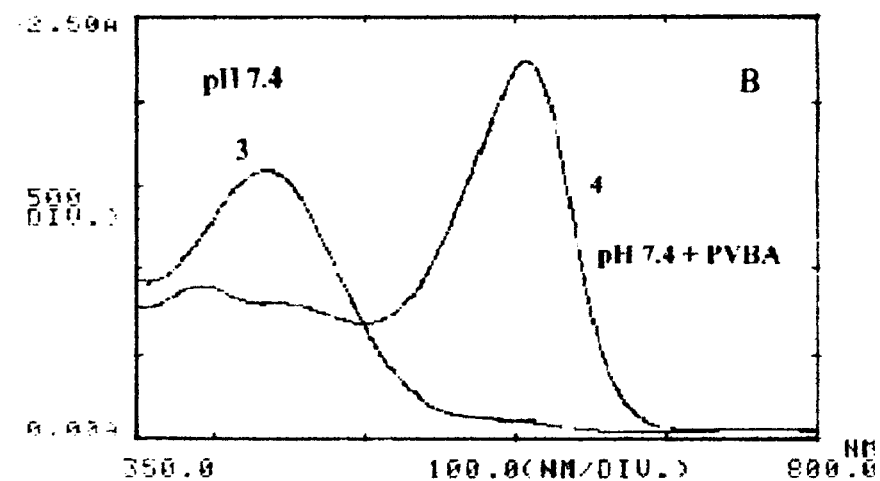

The color response of these compositions is shown in FIGS. 1A and 1B. In FIG. 1A, the spectra of the uncomplexed indicator, thymol blue, at pH 7.4 (yellow) and pH 9.4 (blue) are shown (curves 1–2). In FIG. 1B, the spectra of the uncomplexed and complexed indicator, both at pH 7.4, are shown (curves 3–4). Note that the complexed indicator is blue at pH 7.4.

Example 2

This Example Shows How Increasing TDS Incrementally Converts the Blue Complexed Form of Thymol Blue to the Yellow Uncomplexed Form at pH 7.4

Figure 1C:
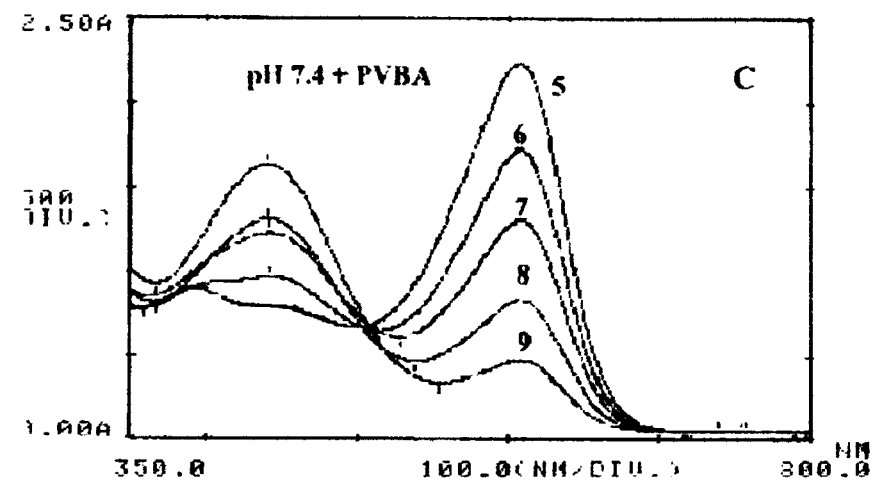

Increasing amounts of TDS, as sodium chloride were added to the composition No. 3 of Example 1. Color of the composition was changed from intense blue to yellow-greenish in the 70–2000 ppm NaCl range. Light absorption was measured. The absorbency of the composition at different increasing TDS levels is shown in FIG. 1C (curves 5–9).

Example 3

Test Strip (Device) Preparation

A test composition was prepared by dissolving the chemicals listed in Table 2 below in distilled water.

TABLE 2

| Reagent composition for dry chemistry test device | |
|---|---|
| Chemical | Amount (g/L) |
| Thymol blue, sodium salt | 0.4 |
| PVBA hydroxide | 4.5 |
| Imidazole | 3.4 |
| Glycolic acid | A sufficient amount to adjust pH to 7.5 |

Ahlstrom filter paper was impregnated with the reagent and dried. The test paper was cut into small pads of 1/5 inch by 1/5 inch and attached to one end of strips of rigid plastic sheet material approximately 1/5 inch wide by 3 inches long. The prepared test strips were activated for 1 second by immersing in standard TDS solutions. Test pad color was read after 15 seconds. The color changed from blue to yellow-green in the 0–5000 ppm TDS range. Reflectance of each activated test pad was measured with a reflectance spectrophotometer. Results are shown in Table 3.

TABLE 3

| TDS test device dose response | | | | | |
|---|---|---|---|---|---|
| TDS ppm as NaCl | 0 | 440 | 1400 | 2880 | 4880 |
| % Reflectance at 610 nm | 7.59 | 10.62 | 16.50 | 23.60 | 29.06 |

Example 4

This Example Demonstrates TDS Test Device Response to Different Ionic Species The procedure of Example 3 was used to prepare test strips. Sample solutions of 1400 ppm of NaCl, $CaCl_2$, $Na_2SO_4$ and $MgCl_2$ were prepared and measured with test strips. A one second dip time and a 15 second read time were used. The color developed was compared with a color chart that was made using standard TDS solutions at 0, 440, 1400, 2880 and 4880 ppm NaCl. A color chart was prepared to permit semiquantitative measurement of TDS samples with the test strip. Colors were selected to match standard TDS concentrations and assigned the numbers to the colors. The numerical values and corresponding TDS levels are as follows: 10 (0 ppm), 20 (400 ppm), 30 (1400 ppm), 40 (2880 ppm) and 50 (4880 ppm). Using this chart, the test device response is expressed in numerical response as shown in Table 4.

TABLE 4

| TDS test device response to different ionic species of samples | | |
|---|---|---|
| TDS Sample, Ionic Species | TDS Gravimetric Sample, ppm | TDS Test Device Result Color Chart Designation |
| NaCl | 1400 | 31 |
| $CaCl_2$ | 1400 | 32 |
| $Na_2SO_4$ | 1400 | 32 |
| $MgCl_2$ | 1400 | 33 |

What is claimed is:

1. A test device for the determination of total dissolved solids in an aqueous sample having a low specific gravity comprising the dried residue of a solution of a test composition, said test composition comprising:

a. a complex of thymol blue and poly(vinylbenzyltrimethylammonium hydroxide);

b. a buffer system for maintaining the mixture of the test composition and the aqueous sample at an exact predetermined pH; and c. a solid water insoluble matrix material, where the dried residue is incorporated into the matrix material.

2. The test device of claim 1, wherein the buffer system comprises a monocarboxylic acid.

3. The test device of claim 2, wherein the monocarboxylic acid is selected from the group consisting of glycolic acid, lactic acid, benzoic acid, and acetic acid.

4. The test device of claim 1, wherein the buffer system comprises a component selected from the group consisting of imidazole, tris(hydroxymethyl)aminomethane, 2-amino-2-methyl-1,3-bis(2-hydroxyethyl)imino tris(hydroxymethyl)methane, and 1,3-bis[tris(hydroxymethyl)methylamino]propane.

5. The test device of claim 1, wherein the buffer system comprises a base component selected from the group consisting of imidazole, tris(hydroxymethyl)aminomethane, 2-amino-2-methyl-1,3-propanediol, bis(2-hydroxyethyl)imino tris(hydroxymethyl)methane, and 1,3-bis[tris(hydroxymethyl)methylamino]propane, and an acid component selected from the group consisting of glycolic acid, lactic acid, benzoic acid, and acetic acid.

6. A test kit for the determination of total dissolved solids in an aqueous sample comprising:

a. test device comprising a water insoluble matrix material incorporated with the dried residue of a test reagent solution comprising thymol blue, and poly(vinylbenzyltrimethylammonium hydroxide);

b. a buffer for maintaining the mixture of the test reagent and the aqueous sample at an exact predetermined pH; and c. a standard for comparing a color produced from contacting the aqueous sample and the test reagent with a standard color produced from contacting a sample having a known concentration of total dissolved solids with the test reagent.

* * * * *